United States Patent
Bausewein et al.

(10) Patent No.: US 7,427,347 B2
(45) Date of Patent: Sep. 23, 2008

(54) METHOD FOR OPERATING A MEASURING PROBE FOR MEASURING A GAS CONCENTRATION

(75) Inventors: Andreas Bausewein, Langenbach (DE); Michael Busch, Ebersbach (DE); Ludwig Schifferl, Pentling (DE)

(73) Assignees: Siemens Aktiengesellschaft, Munich (DE); Daimlerchrysler AG, Stuttgart (DE)

( * ) Notice: Subject to any disclaimer, the term of this patent is extended or adjusted under 35 U.S.C. 154(b) by 766 days.

(21) Appl. No.: 10/802,037

(22) Filed: Mar. 17, 2004

(65) Prior Publication Data
US 2005/0061684 A1  Mar. 24, 2005

(30) Foreign Application Priority Data
Mar. 21, 2003  (DE)  ................. 103 12 732

(51) Int. Cl.
*G01N 27/407*  (2006.01)
(52) U.S. Cl. .................. 205/781; 204/401; 204/425; 73/23.31
(58) Field of Classification Search ................. 204/401, 204/425, 427; 205/781, 784; 73/23.31
See application file for complete search history.

(56) References Cited

U.S. PATENT DOCUMENTS

| 4,167,163 | A | * | 9/1979  | Moder ........................ 123/688 |
| 4,326,318 | A | * | 4/1982  | DeBruin et al. ............. 205/784 |
| 4,707,241 | A |   | 11/1987 | Nakagawa et al. |
| 4,713,166 | A | * | 12/1987 | Kojima et al. ................ 204/425 |
| 4,724,814 | A |   | 2/1988  | Mieno et al. |
| 4,777,922 | A |   | 10/1988 | Mieno et al. |
| 6,071,393 | A | * | 6/2000  | Oshima et al. ............... 204/425 |
| 6,266,993 | B1 |  | 7/2001  | Diehl et al. |
| 6,290,829 | B1 |  | 9/2001  | Kato et al. |

FOREIGN PATENT DOCUMENTS

| DE | 3710154 A1  | 10/1987 |
| DE | 3607400 C2  | 6/1988 |
| DE | 3710221 C2  | 7/1990 |
| DE | 19845927 A1 | 4/2000 |
| DE | 10049685 A1 | 4/2002 |

* cited by examiner

*Primary Examiner*—Kaj K Olsen

(57) ABSTRACT

In a method for operating a measuring probe for measuring a gas concentration in a measuring gas with the aid of a solid electrolyte which conducts oxygen ions and has a measurement cavity for holding the measuring gas, a measuring electrode and an external electrode, a pumping current flowing between the measuring electrode and external electrode transporting oxygen ions from the measuring electrode to the external electrode, the measuring electrode being checked by determining the electrode area effectively available for oxygen diffusion.

10 Claims, 2 Drawing Sheets

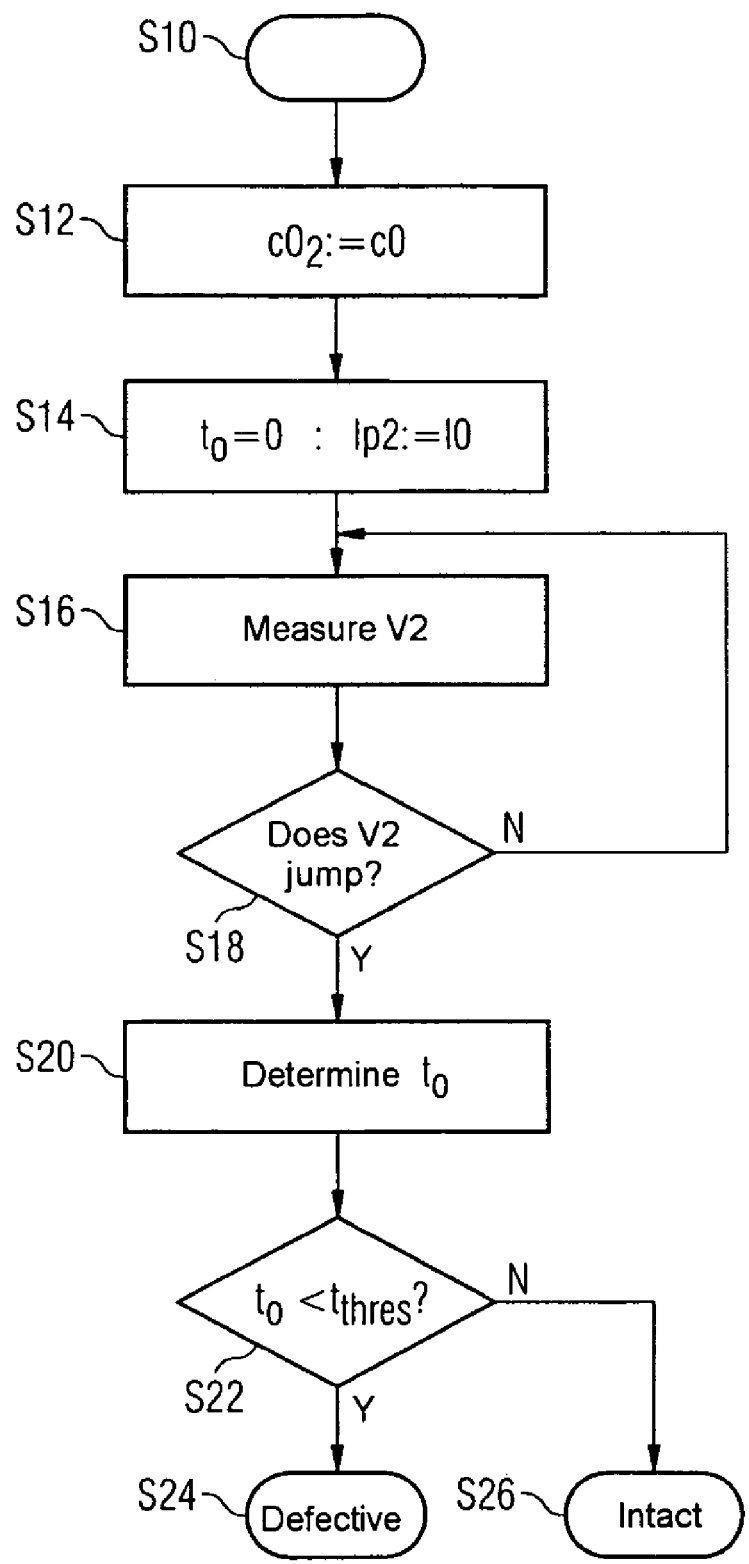

METHOD FOR OPERATING A MEASURING PROBE FOR MEASURING A GAS CONCENTRATION

CLAIM FOR PRIORITY

This application claims the benefit of priority to DE 10312732.1, filed Mar. 21, 2003, the contents of which are hereby incorporated by reference.

TECHNICAL FIELD OF THE INVENTION

The invention relates to a method for operating a measurement probe for measuring a gas concentration in a measuring gas with the aid of a solid electrolyte which conducts oxygen ions and has a measurement cavity for holding the measuring gas, a measuring electrode and an external electrode, a pumping current flowing between the measuring electrode and external electrode transporting oxygen ions from the measuring electrode to the external electrode.

BACKGROUND OF THE INVENTION

It is known for the purpose of measuring the NOx concentration in a measuring gas, for example the exhaust gas of an internal combustion engine, to use a sensor such as is described, for example, in the publication DE 199 07 947 A1. The mode of operation of the sensor is based on the Nernst principle. At temperatures above 350.degree. C., the solid electrolyte material of the sensor is simultaneously a very good oxygen ion conductor and a poor ion conductor with reference to other chemical elements.

Different oxygen concentrations on the two sides of the solid electrolyte lead to different electric potentials of the electrodes arranged on the respective sides. The potential difference then constitutes a measure of the difference in the oxygen concentration on the two sides of the solid electrolyte.

The quantity of remaining oxygen in the exhaust gas fluctuates strongly with a change in the air/fuel ratio, the lambda value. If the air/fuel mixture is in the so-called rich range (lambda value<1), in which the fuel is present in stoichiometric excess, the result is typically a Nernst voltage between the two electrodes of 800 to 1000 mV. For the so-called lean mixtures (lambda value>1), where the oxygen predominates over the air, the result is a Nernst voltage down to approximately 100 mV. Upon transition from rich to lean mixture, the Nernst voltage therefore changes discontinuously in the region about the stoichiometric lambda value 1 by 700 to 800 mV.

The measuring sensor in the abovenamed DE 199 07 947 A1 has two measuring cells in a body made from an oxygen-conducting solid electrolyte. Oxygen is pumped out of the first measuring cell, which is fed the measuring gas via a diffusion barrier, by means of a first pumping current, and a first oxygen concentration is set thereby.

The measuring gas diffuses from the first measuring cell into the second measuring cell via a diffusion barrier. The oxygen content is further lowered in the second measuring cell by means of a second pumping current, and an oxygen concentration is set. NOx is decomposed at a measuring electrode arranged in the second measuring cell, and the oxygen thereby formed is pumped off by means of a third pumping current. The third pumping current then constitutes a measure of the NOx concentration in the measuring gas.

In order to set the pumping current, the Nernst potential at the electrodes is tapped in the respective measuring cells, said potential being determined relative to the oxygen content of a reference gas to which a reference electrode is exposed.

Depending on the tendency to oxidation of the electrode material as a consequence of controller deficiencies or manufacturing fluctuations and/or material tolerances, it can happen that the electrode material oxidizes more or less strongly and changes its volume owing to the incorporation of oxygen. The corruption of the measurement signal associated therewith can have the effect that the emission values prescribed for motor vehicles can no longer be met using a sensor changed in this way.

SUMMARY OF THE INVENTION

The invention relates to developing a generic method such that the reliability of the measured value determined by the measurement probe is increased.

In the invention, the integrity of the measuring electrode is checked by determining the electrode area effectively available for oxygen diffusion.

In one embodiment of the invention, the corrupted measured values stem from a detachment of the electrode material and/or a cover layer lying thereover, owing to mechanical stresses or the tendency of the material to oxidize. The detachment is detected according to the invention by determining the electrode area effectively available for the oxygen diffusion. A range of preferred methods are specified below for this determination.

In another embodiment of the method according to the invention, the measuring electrode is checked by setting a predetermined oxygen concentration in the measurement cavity, impressing a predetermined constant pumping current between the measuring electrode and external electrode, measuring the resulting Nernst potential at the measuring electrode, measuring the period of time until the measured Nernst potential jumps from small to large values, comparing the measured period of time with a predetermined threshold value, and detecting a defect in the measuring electrode when the measured period of time falls below the predetermined threshold value.

It is expedient in this case to select the predetermined constant pumping current to be so large that even in the case of an intact measuring electrode more oxygen is transported from the measuring electrode to the external electrode than can subsequently diffuse into the measuring electrode.

According to another embodiment of the method according to the invention, the measuring electrode is checked by impressing a predetermined constant pumping current between the measuring electrode and external electrode, varying the oxygen concentration in the measurement cavity and measuring the resulting Nernst potential at the measuring electrode, determining the oxygen concentration at which the measured Nernst potential jumps between small and large values, comparing the determined oxygen concentration with a reference value, and detecting a defect in the measuring electrode when the determined oxygen concentration deviates from the reference value by more than a predetermined amount.

The oxygen concentration in the measurement cavity is advantageously determined by measuring the Nernst potential at an auxiliary electrode in the measurement cavity.

In accordance with a further embodiment of the method according to the invention, the measuring electrode is checked by setting a predetermined oxygen concentration in the measurement cavity, impressing a pumping current between the measuring electrode and external electrode that is set such that a predetermined value of the Nernst potential is present at the measuring electrode, varying the oxygen concentration in the measurement cavity and adjusting the pumping current between the measuring electrode and external electrode such that the Nernst potential at the measuring electrode is kept constant, determining the proportionality factor between the pumping current and oxygen concentration, comparing the determined proportionality factor with a reference value, and detecting a defect in the measuring electrode when the determined proportionality factor deviates from the reference value by more than a predetermined amount.

It is preferred when carrying out the method to set two predetermined values of the oxygen concentration in the measurement cavity at which the pumping current is set in each case such that the predetermined value of the Nernst potential is present at the measuring electrode, and the proportionality factor between the pumping current and oxygen concentration is determined from the two values for the pumping current set. Since there is a linear relationship between pumping current and oxygen concentration, two measured values suffice for determining the proportionality factor.

The detachment of a cover layer lying over the measuring electrode is advantageously detected from the fact that the determined proportionality factor exceeds a reference value by more than a predetermined amount. By contrast, the detachment of the cover layer from the measuring electrode generally obtains when the determined proportionality factor falls below the reference value by more than a predetermined amount.

According to yet a further embodiment of the method according to the invention, the measuring electrode is checked by setting a predetermined oxygen concentration in the measurement cavity, impressing a pumping current between the measuring electrode and external electrode that is set such that a predetermined value of the Nernst potential is present at the measuring electrode, comparing the pumping current set with a reference value, and detecting a defect in the measuring electrode when the pumping current set deviates from the reference value by more than a predetermined amount.

In this embodiment, a detachment only of the cover layer of the measuring electrode is detected when the pumping current set exceeds the reference value by more than a predetermined amount. The detachment of cover layer and measuring electrode is seen in the fact that the pumping current set falls below the reference value by more than a predetermined amount.

The integrity of the measuring electrode can advantageously be checked with each start of the measurement probe. Alternatively, or in addition, the measuring electrode can be checked on demand, in particular by a control unit.

BRIEF DESCRIPTION OF THE DRAWINGS

The invention is explained in yet further detail below by way of example with reference to the drawings, in which:

FIG. 2 shows a flowchart for carrying out an operating method according to the invention.

DETAILED DESCRIPTION OF THE INVENTION

Figure 1:
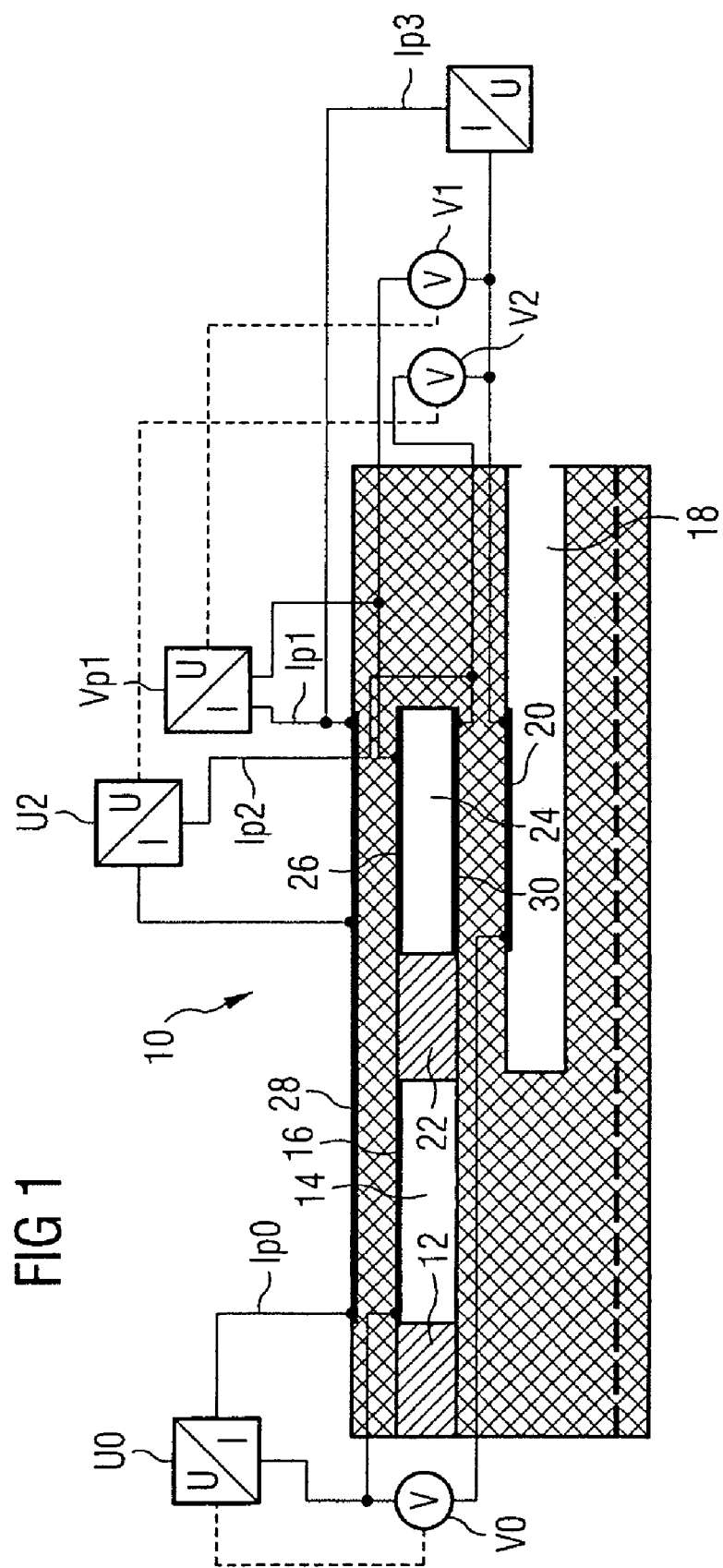
FIG. 1 shows a schematic sectional illustration of an NOx sensor with associated circuitry.

FIG. 1 shows a schematic sectional illustration of an NOx sensor 10 for detecting the NOx concentration in the exhaust duct of an internal combustion engine. The NOx sensor 10 is constructed from a solid electrolyte, in the exemplary embodiment from $ZrO_2$. The exhaust gas to be measured diffuses into a first measuring cell 14 via a diffusion barrier 12.

The oxygen content of the first measuring cell 14 is measured in a known way by tapping a Nernst voltage V0 between a first electrode 16 in the measuring cell 14 and a reference electrode 20 arranged in the reference cell 18. The oxygen content in the first measuring cell 14 is therefore referred to the oxygen content in the reference cell 18.

On the basis of the measured oxygen content in the first measuring cell 14, the voltage-controlled current source U0 is used to adjust, by a first pumping current Ip0, a predetermined oxygen concentration in the first measuring cell 14 in the range of a few ppm.

The measuring gas diffuses from the first measuring cell 14 into a second measuring cell 24 via a second diffusion barrier 22. In the second measuring cell 24, a second voltage-controlled current source U1 lowers the oxygen content of the measuring gas to values in the range of a few $10^{-3}$ ppm by means of a second Nernst voltage V1 between a second electrode 26 and the reference electrode 20. For this purpose, the current source U1 drives a second pumping current Ip1 between the second electrode 26 and an external electrode 28.

NOx is now catalytically decomposed at a measuring electrode 30 in the second measuring cell 24, and the oxygen produced is transported to the external electrode 28 from the measuring electrode 30 via a third pumping current Ip2. The oxygen content in the second measuring cell 24 is lowered by the second pumping current Ip1 so far that the third pumping current Ip2 is substantially borne only by the oxygen ions that originate from the decomposition of NOx at the measuring electrode 30. The third pumping current Ip2 is therefore a measure of the NOx concentration in the second measuring cell 24, and thus also in the exhaust gas to be measured.

FIG. 2 shows a flowchart for carrying out an operating method according to the invention, in which the integrity of the measuring electrode 30 is checked, for example on demand by a control unit.

For this purpose, after a step S10, in which the method is started, there is firstly set in a step S12 in the second measuring cell 24 a predetermined oxygen concentration that is also set in the measuring electrode 30 with a third pumping current Ip2 switched off for the time being. The oxygen concentration is selected to be so high, 2500 ppm in the exemplary embodiment, that it is possible to neglect an NOx concentration that may be present, for example 500 ppm, by comparison therewith as regards the content of oxygen atoms.

A predetermined constant pumping current Ip2=10 between the measuring electrode 30 and external electrode 28 is then driven at an instant t0=0 in a step S14, and the resulting Nernst potential V2 at the measuring electrode 30 is measured in step S16. The incipient pumping activity removes oxygen from the electrode 30, it also being possible for oxygen to diffuse subsequently into the measuring electrode 30 from the gas space via a cover layer of the measuring electrode 30 through the diffusion-limiting cover layer.

It is now checked in a step S18 whether the measured Nernst potential V2 jumps from small to large values, and the period of time to up to this jump is determined in step S20. The period of time t0 thus determined is then compared in a step S22 with a predetermined threshold value t_thres. In the event of a reduced effective boundary layer owing to electrode detachment, that is to say of a diminished gas phase/electrode-material/solid electrolyte interface, the volume of the measuring electrode 30 is also reduced together with the contact surface to the electrolyte material. Consequently, the oxygen quantity is also smaller inside the measuring electrode 30 and can be pumped out more quickly by means of a constant pumping current Ip2 than in the case of a larger electrode area.

It goes without saying that the pumping current Ip2 is selected to be so large that even in the case of an intact measuring electrode it is possible for more oxygen to be removed than can subsequently diffuse.

The oxygen quantity inside the measuring electrode 30 requires a defined charge quantity during transport as oxygen ions through the solid electrolyte that corresponds to the integral over Ip2*dt, that is to say to the value I0*t0, given a constant current. A complete removal of the oxygen from the measuring electrode 30 is detected via the Nernst potential V2, which then jumps suddenly from small values, approximately 100 mV in the exemplary embodiment, to large values, approximately 800 to 1000 mV in the exemplary embodiment. If, because of an electrode detachment, the electrode area is now reduced, the measuring electrode thus no longer being intact, t0 will lie, given a constant pumping current I0, below a predetermined threshold value t_thres that was determined previously as limiting value for the detection of a defective electrode.

Consequently, a defect in the measuring electrode is detected in a step S24 when the measured period of time t0 falls below the predetermined threshold value t_thres. Otherwise, the electrode is evaluated as intact in step S26.

According to another exemplary embodiment of the operating method, instead of the approach of switching on the second pumping current Ip2 at a specific time instant and determining the period of time until the jump in the Nernst potential, the oxygen concentration is now varied in the second measuring cell 24 given a constant pumping current Ip2. If the oxygen concentration is now tuned, Ip2 therefore follows the external oxygen concentration. Since the quantity of oxygen that can subsequently diffuse in the event of a reduced effective surface of the measuring electrode is smaller than given an intact electrode, the Nernst potential V2 already jumps at a higher oxygen concentration than in the case of an intact electrode. The oxygen concentration in the second measuring cell 24 is measured in the exemplary embodiment via the Nernst potential V1 of the second electrode 26, and so in the event of a defective electrode 30 the jumping point of the Nernst potential V2 is at a value of the Nernst potential V1 differing from the reference value. It goes without saying that a defect is not diagnosed until an established permitted deviation from the reference value is exceeded.

In a further exemplary embodiment of the operating method according to the invention, the oxygen concentration in the second measuring cell 24 is set to a predetermined value, while the pumping current Ip2 is controlled such that a predetermined value of the Nernst potential is present at the measuring electrode 30. If the oxygen concentration in the second measuring cell 24 is now tuned and Ip2 is adjusted in the process such that the Nernst potential remains constant at the measuring electrode, Ip2 then follows the external oxygen concentration. Since the quantity of oxygen that can subsequently diffuse given a reduced effective surface of the measuring electrode is smaller than given an intact electrode, in the case of a reduced electrode surface a smaller proportionality factor of Ip2 in relation to the oxygen concentration is set up in the second measuring cell 24 than for the intact measuring electrode 30.

Two measuring points suffice for determining the proportionality factor because of the linear relationship between the pumping current Ip2 and oxygen concentration. If only the cover layer of the measuring electrode is detached owing to a crack, a substantially larger proportionality factor (approximately twice as large in the exemplary embodiment) than for an intact electrode results, in a fashion largely independent of the size of the crack. If, by contrast, the cover layer and measuring electrode are detached jointly, a smaller proportionality factor, and an offset in the current/concentration relationship that is caused by the brittle cover layer is seen because of the smaller area of the measuring electrode 30.

The integrity of the measuring electrode 30 can also be determined with the aid of a measurement given only a single oxygen concentration. For this purpose, an increased oxygen concentration, 500 ppm to 750 ppm in the exemplary embodiment, is set and the pumping current Ip2 required to reach a predetermined Nernst potential is measured. A mean value that serves as reference value results in the case of intact electrode 30. Detachment of only the cover layer results in a higher current value, while detachment of the cover layer and measuring electrode results in a lower current value. For example, if the reference value is exceeded by 30% or more, a detachment only of the cover layer is detected, and if the reference value has fallen below by 30% or more, detachment of the cover layer and measuring electrode is detected.

The invention claimed is:

1. A method for operating a measurement probe for measuring a gas concentration in a measuring gas using a solid electrolyte which conducts oxygen ions and has a measurement cavity for holding the measuring gas, a measuring electrode and an external electrode, a pumping current flowing between the measuring electrode and external electrode transporting oxygen ions from the measuring electrode to the external electrode, comprising:

checking the measuring electrode by determining the electrode area effectively available for oxygen diffusion, or a value dependent thereon wherein the measuring electrode is checked by:

setting a predetermined oxygen concentration in the measurement cavity, impressing a predetermined constant pumping current between the measuring electrode and external electrode, and measuring the resulting Nernst potential at the measuring electrode, measuring the period of time until the measured Nernst potential jumps from small to large values, comparing the measured period of time with a predetermined threshold value, and establishing a defect in the measuring electrode when the measured period of time falls below the predetermined threshold value.

2. The method as claimed in claim 1, wherein the predetermined constant pumping current is selected to be large such that in the case of an intact measuring electrode more oxygen is transported from the measuring electrode to the external electrode than can subsequently diffuse into the measuring electrode.

3. The method as claimed in claim 1, wherein the measuring electrode is checked with each start of operation of the measuring probe.

4. The method as claimed in claim 1, wherein the measuring electrode is checked on demand, in particular by a control unit.

5. A method for operating a measurement probe for measuring a gas concentration in a measuring gas using a solid electrolyte which conducts oxygen ions and has a measurement cavity for holding the measuring gas, a measuring electrode and an external electrode, a pumping current flowing between the measuring electrode and external electrode transporting oxygen ions from the measuring electrode to the external electrode, comprising:

checking the measuring electrode by determining the electrode area effectively available for oxygen diffusion, or a value dependent thereon wherein the measuring electrode is checked by:
  impressing a predetermined constant pumping current between the measuring electrode and external electrode,
  varying the oxygen concentration in the measurement cavity and measuring the resulting Nernst potential at the measuring electrode,
  determining the oxygen concentration at which the measured Nernst potential jumps between small and large values,
  comparing the determined oxygen concentration with a reference value, and
  establishing a defect in the measuring electrode when the determined oxygen concentration deviates from the reference value by more than a predetermined amount.

6. The method as claimed in claim 5, wherein the oxygen concentration in the measurement cavity is determined by measuring the Nernst potential at an auxiliary electrode in the measurement cavity.

7. A method for operating a measurement probe for measuring a gas concentration in a measuring gas using a solid electrolyte which conducts oxygen ions and has a measurement cavity for holding the measuring gas, a measuring electrode and an external electrode, a pumping current flowing between the measuring electrode and external electrode transporting oxygen ions from the measuring electrode to the external electrode, comprising:
  checking the measuring electrode by determining the electrode area effectively available for oxygen diffusion, or a value dependent thereon wherein the measuring electrode is checked by:
    setting a predetermined oxygen concentration in the measurement cavity,
    impressing a pumping current between the measuring electrode and external electrode that is set such that a predetermined value of the Nernst potential is present at the measuring electrode,
    varying the oxygen concentration in the measurement cavity and adjusting the pumping current between the measuring electrode and external electrode such that the Nernst potential at the measuring electrode is kept constant,
    determining the proportionality factor between the pumping current and oxygen concentration,
    comparing the determined proportionality factor with a reference value, and
    establishing a defect in the measuring electrode when the determined proportionality factor deviates from the reference value by more than a predetermined amount.

8. The method as claimed in claim 7, wherein two predetermined values of the oxygen concentration are set in the measurement cavity at which the pumping current is set in each case such that the predetermined value of the Nernst potential is present at the measuring electrode, and the proportionality factor between the pumping current and oxygen concentration is determined from the two values for the pumping current set.

9. The method as claimed in claim 7, wherein a detachment of a cover layer lying over the measuring electrode is established when the determined proportionality factor exceeds a reference value by more than a predetermined amount.

10. The method as claimed in claim 7, wherein a detachment of a cover layer lying over the measuring electrode and of the measuring electrode is established when the determined proportionality factor falls below the reference value by more than a predetermined amount.

* * * * *